(12) United States Patent
Lye

(10) Patent No.: US 10,271,963 B2
(45) Date of Patent: Apr. 30, 2019

(54) REFERENCING APPARATUS AND ASSOCIATED METHODS

(71) Applicant: INERTIAL ORTHOPAEDIC NAVIGATION SOLUTIONS PTY LTD, Brookvale, New South Wales (AU)

(72) Inventor: Robert Lye, Brookvale (AU)

(73) Assignee: INERTIAL ORTHOPAEDIC NAVIGATION SOLUTIONS PTY LTD, Brookvale, New South Wales (AU)

( * ) Notice: Subject to any disclaimer, the term of this patent is extended or adjusted under 35 U.S.C. 154(b) by 596 days.

(21) Appl. No.: 14/407,544

(22) PCT Filed: Jun. 28, 2013

(86) PCT No.: PCT/AU2013/000714
§ 371 (c)(1),
(2) Date: Dec. 12, 2014

(87) PCT Pub. No.: WO2014/000054
PCT Pub. Date: Jan. 3, 2014

(65) Prior Publication Data
US 2015/0150692 A1 Jun. 4, 2015

(30) Foreign Application Priority Data

Jun. 28, 2012 (AU) ................................ 2012902750
Apr. 12, 2013 (AU) ................................ 2013204941

(51) Int. Cl.
*A61B 46/00* (2016.01)
*A61F 2/46* (2006.01)
(Continued)

(52) U.S. Cl.
CPC ............ *A61F 2/4609* (2013.01); *A61B 34/20* (2016.02); *A61B 46/00* (2016.02); *A61B 17/1746* (2013.01);
(Continued)

(58) Field of Classification Search
CPC ...... A61B 2034/107; A61B 2034/2068; A61B 2090/0807; A61B 2090/363;
(Continued)

(56) References Cited

U.S. PATENT DOCUMENTS

RE41,912 E * 11/2010 Parker ................ A61B 5/14552
600/310
2006/0184177 A1 8/2006 Echeverri
(Continued)

FOREIGN PATENT DOCUMENTS

| JP | 2004-089653 | | 3/2004 | |
|---|---|---|---|---|
| WO | 2010 031111 | | 3/2010 | |
| WO | WO 2010145769 | * | 12/2010 | ............... A61F 2/46 |

OTHER PUBLICATIONS

International Search Report dated Nov. 7, 2013 for PCT/AU2013/000714.

*Primary Examiner* — Samuel S Hanna
(74) *Attorney, Agent, or Firm* — Gottlieb, Rackman & Reisman, P.C.

(57) ABSTRACT

The invention relates to a referencing apparatus for application onto a patient at least partially covered by surgical drapes. The referencing apparatus includes a plurality of locking elements shaped for engagement with the surgical drapes. The surgical drapes are disposed intermediate the plurality of locking elements and a respective plurality of predefined anatomical sites on the patient. The engagement causes a docking system disposed on the referencing appa-
(Continued)

ratus to assume a reference orientation relative to the plurality of predefined anatomical sites.

12 Claims, 6 Drawing Sheets

(51) Int. Cl.
*A61B 34/20* (2016.01)
*A61B 17/17* (2006.01)
*A61B 90/00* (2016.01)
*A61B 34/10* (2016.01)

(52) U.S. Cl.
CPC ......... *A61B 90/37* (2016.02); *A61B 2034/107* (2016.02); *A61B 2034/2048* (2016.02); *A61B 2034/2068* (2016.02); *A61B 2090/0807* (2016.02); *A61B 2090/363* (2016.02); *A61B 2090/3983* (2016.02)

(58) Field of Classification Search
CPC ............ A61B 2090/3983; A61B 34/20; A61B 2034/2048; A61B 2017/0212; A61B 2018/1407; A61B 46/00; A61B 46/10; A61B 46/20; A61B 46/304
See application file for complete search history.

(56) References Cited

U.S. PATENT DOCUMENTS

| | | | |
|---|---|---|---|
| 2010/0174415 A1 | 7/2010 | Humayun | |
| 2012/0143268 A1* | 6/2012 | Burroughs | ............. A61B 34/20 606/86 R |

* cited by examiner

REFERENCING APPARATUS AND ASSOCIATED METHODS

FIELD OF THE INVENTION

The present invention relates to surgical implements and surgical methods and in particular to a referencing apparatus that may be applied to a patient prior to, or during, surgical procedures, for example surgery involving prosthetic components.

BACKGROUND

The discussion of the prior art within this specification is not, and should not be taken as, an admission of the extent of common general knowledge in the field of the invention. Rather, the discussion of the prior art is provided merely to assist the addressee to understand the invention and is included without prejudice.

Whilst the following discussion is with respect to hip replacement surgery, a person skilled in the art will appreciate that the present invention is not limited to this particular field of use and may be adapted to use with any bone structure or various types of surgery.

Hip replacement surgery involves the use of a prosthetic cup (acetabular cup) or a prosthetic ball (femoral stems) or both to restore the ball and cup joint functionality of the hip. The ball and cup joint enables the hip to rotate in different directions to various degrees (in contrast to the relatively limited rotation of a knee joint).

Historically, hip replacement (arthroplasty) surgery required up to a 40 cm (7 to 12 inches) curved incision to provide sufficient access for the surgeon to manually access and manipulate the hip and femur. A prosthetic cup was attached to the hip socket or the head of the femur removed and replaced with a prosthetic ball, or both.

After the incision is made, the ligaments and muscles are separated to allow the surgeon access to the bones of the hip joint. It is typically this part of the surgery that makes the ligaments and muscles somewhat weak after surgery. Until they heal, which often takes about a month to six weeks, the patient must follow special hip precautions to prevent dislocation of the new hip joint.

Typical steps in hip replacement surgery include the following:

Removing the Femoral Head: Once the hip joint is entered, the femoral head is dislocated from the acetabulum. Then the femoral head is removed by cutting through the femoral neck with a power saw.

Reaming the Acetabulum: After the femoral head is removed, the cartilage is removed from the acetabulum using a power drill and a special reamer. The reamer forms the bone in a hemispherical shape to exactly fit the metal shell of the acetabular component.

Inserting the Acetabular Component: A trial component, which is an exact duplicate of the patient's hip prosthesis, is used to ensure that the joint received will be the right size and fit. Once the right size and shape is determined for the acetabulum, the acetabular component is inserted into place. In the uncemented variety of artificial hip replacement, the metal shell is simply held in place by the tightness of the fit or with screws to hold the metal shell in place. In the cemented variety, a special epoxy type cement is used to "glue" the acetabular component to the bone.

Preparing the Femoral Canal: To begin replacing the femoral head, special rasps are used to shape and hollow out the femur to the exact shape of the metal stein of the femoral component. Once again, a trial component is used to ensure the correct size and shape. The surgeon will also test the movement of the hip joint.

Inserting the Femoral Stem: Once the size and shape of the canal exactly fit the femoral component, the stem is inserted into the femoral canal. Again, in the uncemented variety of femoral component the stem is held in place by the tightness of the fit into the bone (similar to the friction that holds a nail driven into a hole drilled into wooden board—with a slightly smaller diameter than the nail). In the cemented variety, the femoral canal is rasped to a size slightly larger than the femoral stem. Then the epoxy type cement is used to bond the metal stem to the bone.

Attaching the Femoral Head: The metal ball that replaces the femoral head is attached to the femoral stem.

The Completed Hip Replacement: Before the incision is closed, an x-ray is taken to make sure the new prosthesis is in the correct position.

Such surgery had a number of problems including:

a hospital stay of three days or more, post-operative pain and weeks of rehabilitation;

each cm of incision has a tenfold increase in the risks of blood clotting and infection post surgery;

the surgeon was reliant on his experience and eye to ensure accurate placement of the cup into the three dimensional hip socket and alignment of the cup with the ball/femur to enable proper function of the joint. Misalignment may lead to post operative complication such as misalignment of the leg, incorrect leg length and/or incorrect soft tissue tension. The long term effects of misaligned prosthetic components can also include accelerated wear of the components, aseptic loosening of the components and potentially early repetition of the surgery.

Attempts to overcome these problems include:

WO 2003/037192 which discloses a jib (impaction tool) for use in bone surgery and thus enables the use of a smaller incision. For hip replacement surgery, the jig enables the use of a 4 to 7 cm (2 to 3 inch) incision, i.e. keyhole surgery. Other benefits include a shorter stay in hospital, less blood loss, less pain, fewer postoperative dislocations and faster recovery; and WO 2003/046475 which discloses a gauge to assist the surgeon with accurate placement of a prosthetic when using a jig in keyhole surgery as the surgeon is no longer able to see the fit of the cup into the hip socket or the fit between the ball and cup.

The gauge provided in WO 2005/0464175 has enabled efficient use of the impaction tool of WO 2003/037192. Commercial examples include the NilNav Hip System available from MAC Surgical. However, the gauge only works in two dimensions and there is still a heavy reliance on the surgeon's and experience for optimal placement of the cup into the hip.

A further attempt to overcome these problems was provided by WO 2010/031111, the contents of which are hereby incorporated in their entirety into this specification by way of cross reference. This prior art document discloses a brace (3) in the form of a clamp that is attachable to a patient to define a reference point relative to the patient's anatomy. This prior art clamp has a another of pads (14, 16, 17 and 18) that are positioned against various points of the patent's anatomy. However, it has been appreciated by the present inventor that this clamp is likely to be obstructive to at least some surgical procedures and does not readily accommodate the surgical drapes that are typically used hi many surgical settings.

SUMMARY OF THE INVENTION

According to a first aspect of the invention there is provided a referencing apparatus for application onto a patient at least partially covered by surgical drapes, the referencing apparatus including a plurality of locating elements shaped for engagement with the surgical drapes such that the surgical drapes are disposed intermediate the plurality of locating elements and a respective plurality of predefined anatomical sites on the patient and whereby, in use, the apparatus is shaped such that said engagement causes a docking station disposed on the referencing apparatus to assume a reference orientation relative to the plurality of predefined anatomical sites, wherein at least one of the locating elements defines a cavity sized to receive a projection of the surgical drapes caused by the respective anatomical site.

In this embodiment the at least one locating element is a circular loop having an interior defining said cavity and having a diameter of between 30 mm and 70 mm. Preferably at least one of the loops is attached to an arcuate member and the arcuate member is attachable to a frame. Optionally, the arcuate member may be rotatably attachable to the frame so as to define an axis of rotation of the arcuate member. The at least one loop attached to an arcuate member may define a centre that is in axial alignment with an axis of rotation of the arcuate member to which it is attached. Preferably the arcuate member has a radius of curvature of between 40 mm and 80 mm and it is attachable to a slot disposed within the frame such that an attachment position of the arcuate member to the frame is selectively adjustable. Preferably the slot has a length of between 60 mm and 120 mm. The arcuate member may be attachable to the slot by a clamping action provided by a threaded fastener. Preferably the frame is substantially "T" shaped and the docking station is disposed substantially at an intersection of the "T" shape. Preferably proximal ends of three elongate members are respectively attachable adjacent three extremities of the "T" shaped frame and three loops are respectively attached to distal ends of the three elongate members and at least one, and more preferably two, of the elongate members is the arcuate member.

In an embodiment an electronic orientation monitor is dockable with the docking station in either a first docking configuration or a second docking configuration. In this embodiment the first docking configuration defines a first orientation of the electronic orientation monitor relative to the referencing apparatus and a second docking configuration defines a second orientation of the electronic orientation monitor relative to the referencing apparatus. Preferably the first and second docking configurations are respectively defined by first and second holes, each being shaped to receive a shaft extending from the electronic orientation monitor.

An embodiment of the apparatus is configured to solely engage the drapes anterior to the patient.

According to a second aspect of the invention there is provided a method of using a referencing apparatus as described above to calibrate an electronic orientation monitor, the method including the steps of:

positioning surgical drapes onto a patient;

engaging the plurality of locating elements against the surgical drapes such that the surgical drapes are disposed intermediate the plurality of locating elements and a respective plurality of predefined anatomical sites on the patient so as to cause a docking station disposed on the referencing apparatus to assume a reference orientation relative to the plurality of predefined anatomical sites;

docking the electronic orientation monitor with the docking station so as to orient the electronic orientation monitor in a reference orientation; and calibrating the electronic orientation monitor.

According to a third aspect of the invention there is provided a method of using a referencing apparatus as an aid in the insertion of a prosthetic component into an acetabulum of a patient's pelvis, the method including the steps of:

providing, a referencing apparatus having first, second and third locating elements;

positioning surgical drapes onto the patient;

pressing the referencing apparatus into engagement with the surgical drapes such that the surgical drapes are disposed intermediate the first locating element and a right band anterior superior iliac spine of the patient and such that the surgical drapes are disposed intermediate the second locating element and a pubic crest of the patient and such that the surgical drapes are disposed intermediate the third locating element and a left hand anterior superior iliac spine of the patient so as to cause a docking station disposed on the referencing apparatus to assume a reference orientation relative to the patient's pelvis;

docking an electronic orientation monitor with the decking station so as to orient the electronic orientation monitor in a reference orientation and calibrating the electronic orientation monitor;

attaching the electronic orientation monitor to an insertion implement having the prosthetic component disposed thereon;

manipulating an insertion implement into a position whereby the prosthetic component is adjacent the acetabulum; and using the electronic orientation monitor to guide an orientation of the insertion implement such that an orientation of the electronic orientation monitor assumes a predefined relationship to the reference orientation; and inserting the prosthetic component into the acetabulum.

Preferably the referencing apparatus is disposed anterior to the patient during the steps of pressing the referencing apparatus into engagement with the surgical drapes and during calibration of the electronic orientation monitor.

Preferably an anterior approach is used for surgical access to the patent's acetabulum and the patient lies in a time up position during the method's steps.

BRIEF DESCRIPTION OF THE DRAWINGS

Embodiments of the invention will now be described, by way of example only, with reference to the accompanying drawings, in which.

DETAILED DESCRIPTION OF THE PREFERRED EMBODIMENTS

Figure 1:
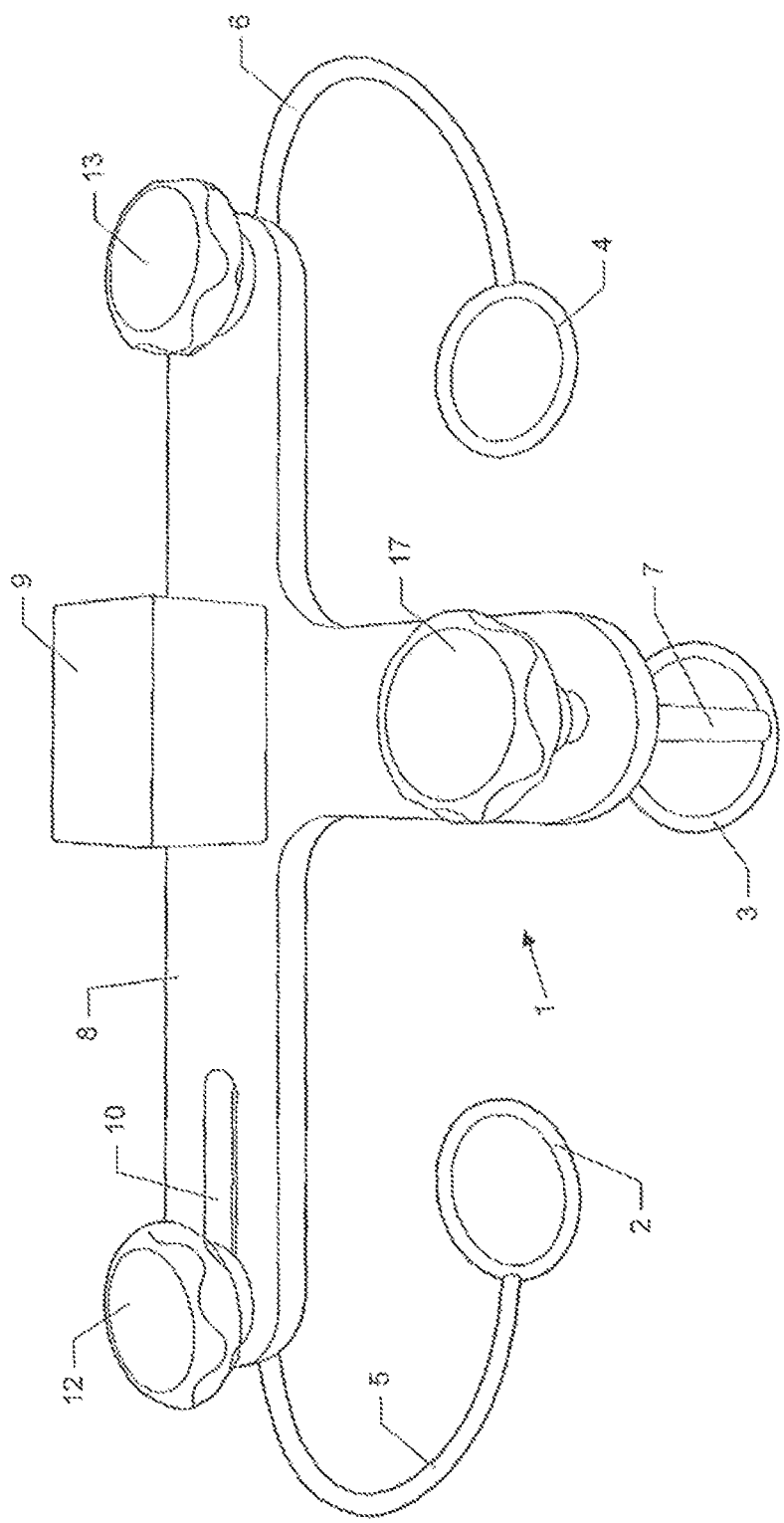
FIG. 1 is a top side perspective view of an embodiment of the referencing apparatus according to the invention.
Figure 2:
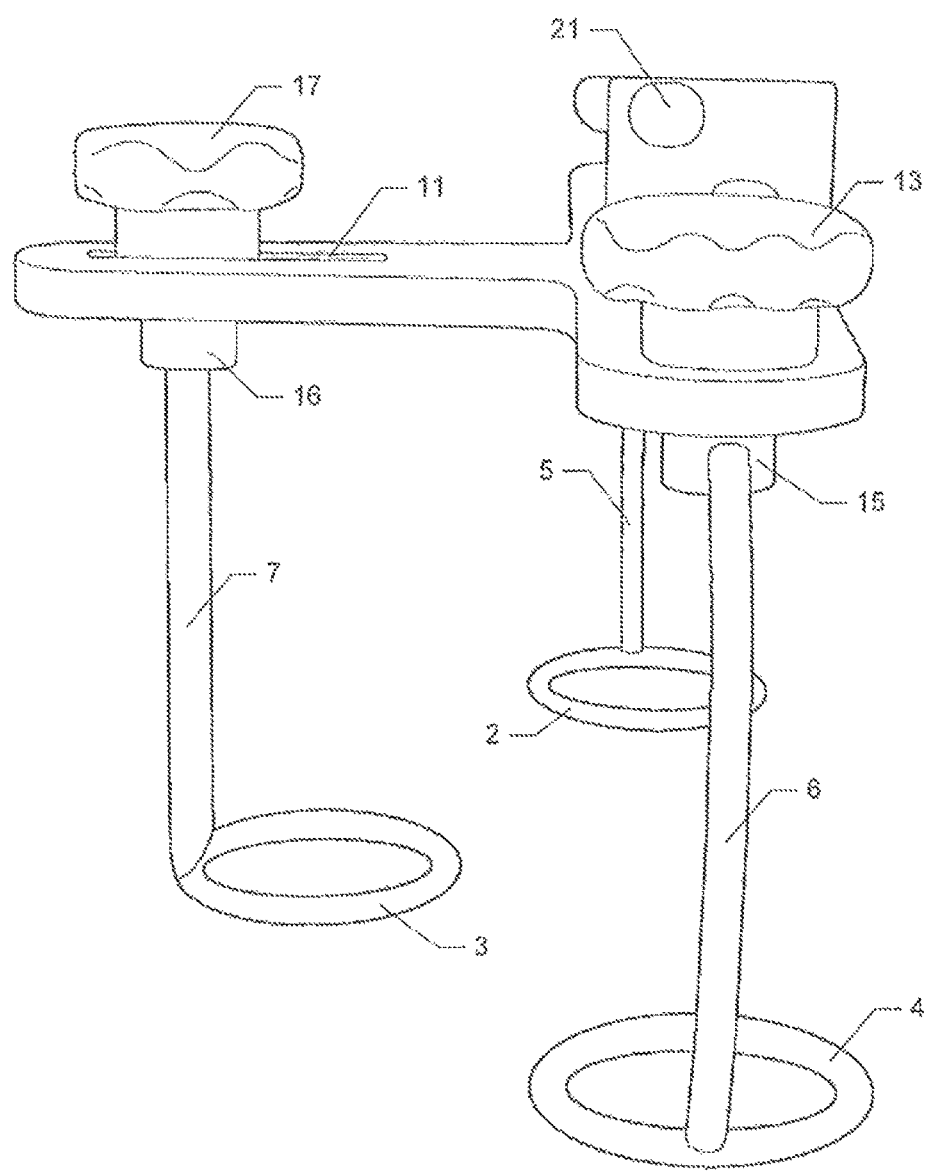
FIG. 2 is a left hand side perspective view of the embodiment of FIG. 1.

Referring to the drawings, the referencing apparatus 1 is for application onto it patient at least partially covered by surgical drapes. Typically the patient lies on the surgical table in a face up position (i.e. the patient lies on his or her back). The surgical drapes are positioned on the patient prior to the surgery so as to cover the general region of the patient that is proposed to be operated upon, with an aperture in the drapes being positioned over the proposed site of the surgical incision. In some instances a surgeon may decide against the use of surgical drapes, in which case alternatives, such as cling film for example, may be used instead. The scope of the term "drapes" as used in this patent specification, including in the claims, is to be construed sufficiently broadly so as to include such alternatives This detailed description shall describe the use of the referencing apparatus 1 as an aid in the insertion of a prosthetic component in the form of an acetabular cup, into a reamed acetabulum of a patient's pelvis wherein an anterior approach is used for surgical access the patent's acetabulum. An important part of this process is the use of the referencing apparatus 1 to calibrate an electronic orientation monitor, which may be as per that disclosed in WO 2010/031111, the contents of which have been incorporated in their entirety into this specification by way of cross reference. However it will be appreciated by those skilled in the art that the invention may be used in other surgical contexts.

The referencing apparatus 1 has a 'T'-shaped frame 8 with a docking station 9 disposed at the intersection of the 'T' shape. The frame 8 defines two slots 10 and 11 disposed adjacent two of the extremities of the 'T' shape. Each of the slots 10 and 11 has a length of between 60 mm and 120 mm and in one embodiment each of their lengths is 70 mm and in another embodiment each of their lengths is 100 mm.

The referencing apparatus 1 has three locating elements, which are each in the shape of circular loops 2, 3 and 4. Each of the loops 2, 3 and 4 has a diameter of between 30 mm and 70 mm and in the illustrated embodiment this diameter is 50 mm. As will be described in more detail below, each of these loops 2, 3 and 4 is sized to receive a projection of the surgical drapes caused by engagement with an anatomical site.

The first and third loops 2 and 4 are each attached to respective distal ends of arcuate members 5 and 6. The radius of curvature of each of the arcuate members 5 and 6 is between 40 mm and 80 mm and is 60 mm in the illustrated embodiment. The curvature of members 5 and 6 provides clearance for situations in which the referencing apparatus 1 is to be used on an overweight or obese patient having stomach fat deposits that would foul against the members 5 and 6 if they were straight. The proximal end of arcuate member 5 is attachable to the frame 8 at slot 10.

The proximal end of arcuate member 6 is attachable to the frame 8 at the extremity of the 'T' shaped frame 8 that does not have a slot 10 or 11. Rather, an aperture is disposed adjacent this extremity, through which the proximal end of arcuate member 6 extends. Screw threads extending to flanges 14 and 15 are respectively provided on the proximal ends of the arcuate members 5 and 6. Screwing threaded fasteners 12 and 13 respectively onto the proximal ends of arcuate members 5 and 6 causes flanges 14 and 15 to engage against the lower side of the frame 8 so as to provide a clamping action that attaches the arcuate members 5 and 6 onto the frame 8.

If the user wishes to adjust the position of the first loop 2 relative to the frame 8, it is merely necessary to loosen the threaded fastener 12, then slide the proximal end of arcuate member 5 along slot 10 until the loop 2 is in the desired position, and then retighten the threaded fastener 12. This adjustability of the attachment position of the arcuate member 5 on the frame allows the separation distance between loops 2 and 4 to be adjusted to match the separation distance between the patient's left anterior superior iliac spine and the patient's right anterior superior iliac spine.

It wilt be appreciated that loosening of threaded fastener 12 also allows far rotation of arcuate member 5 about an axis of rotation that is orthogonal to the upper surface of the frame 8. Hence, if the user wishes to adjust the position of the clearance provided by the curvature of arcuate member 5, then the user merely loosens threaded fastener 12, rotates arcuate member 5 until the curvature is in the desired position and then retightens threaded fastener 12. Doing so does not re-position the loop 2 relative to the frame 8 because the centre of loop 2 is in axial alignment with the axis of rotation of the arcuate member 5. Similarly, it is possible to adjust the position of the clearance provided by the curvature of arcuate member 6 by loosening threaded member 13, rotating arcuate member 6, then re-tightening threaded member 13. This does not reposition loop 4 because its centre is in axial alignment with the axis of rotation of the arcuate member 6.

The second loop 3 is attached to the distal end of a linear elongate member 7. The proximate end of member 7 is attachable to the frame 8 at slot 11. A screw thread extending to a flange 16 is provided on the proximal end of member 7. This allows a threaded fastener 17 to be screwed onto the proximal end of member 7 to thereby cause flange 16 to engage against the lower side of the frame 8 so as to clamp the member 7 onto the flume 8. The position of the second loop 3 can be adjusted by loosening threaded fastener 17, then sliding the proximal end of member 7 along slot 11 until loop 3 is in the desired position and then re-tightening threaded fastener 17. In other words, the adjustability given by slots 10 and 11 allows the referencing apparatus 1 to be used on patient's having variously sized pelvises.

The shape of each of the loops 2, 3 and 4 allows for engagement with the surgical drapes such that the surgical drapes are disposed intermediate the three loops and three respective predefined anatomical sites on the patient. In use, the surgeon and/or an assistant uses their fingers to apply pressure to the surgical drapes to feel for the approximate positions of the predefined anatomical sites, which are the patient's left and right anterior superior iliac spine and the patient's pubic crest. It has been appreciated by the inventor that these anatomical sites may be readily discerned through the surgical drapes in this manner. Once these approximate positions are known the first loop 2 is positioned on the surgical drapes centred above the patient's right hand anterior superior iliac spine. The second loop 3 is positioned on the surgical drapes centred above the patient's pubic crest and the third loop 4 is positioned on the surgical drapes centred above the patient's left hand anterior superior iliac spine.

Once the referencing apparatus 1 is positioned as described in the preceding paragraph the surgeon and/or an assistant presses the referencing apparatus 1 into engagement with the surgical drapes. The anatomical sites have bony projections that become more prominent when the loops 2, and 3 and 4 are pressed against them. This causes the surgical drapes at those sites to project into the cavities defined by the interior of each of the loops 2, 3 and 4. This engagement causes the docking station 9 to assume a reference orientation relative to the three predefined anatomical sites.

Figure 3:
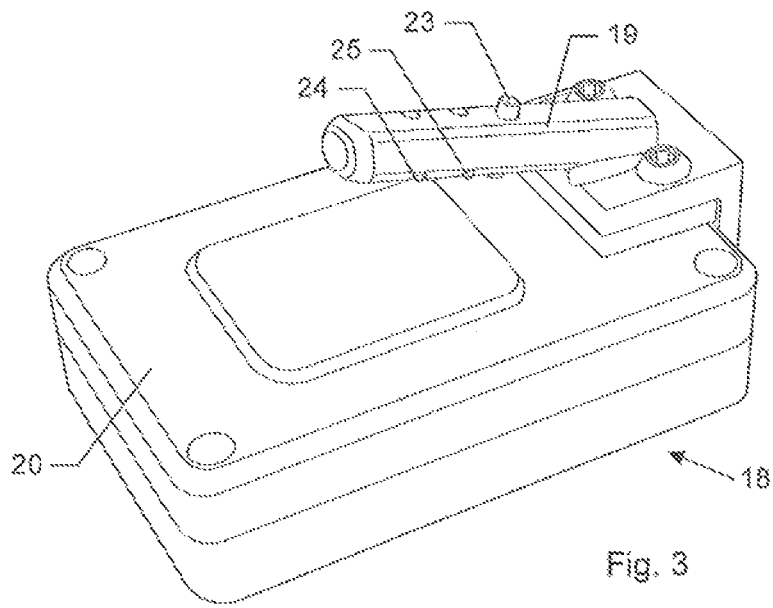
FIG. 3 underside perspective view of an embodiment of an electronic orientation monitor for use with the brace of FIG. 1.
Figure 4:
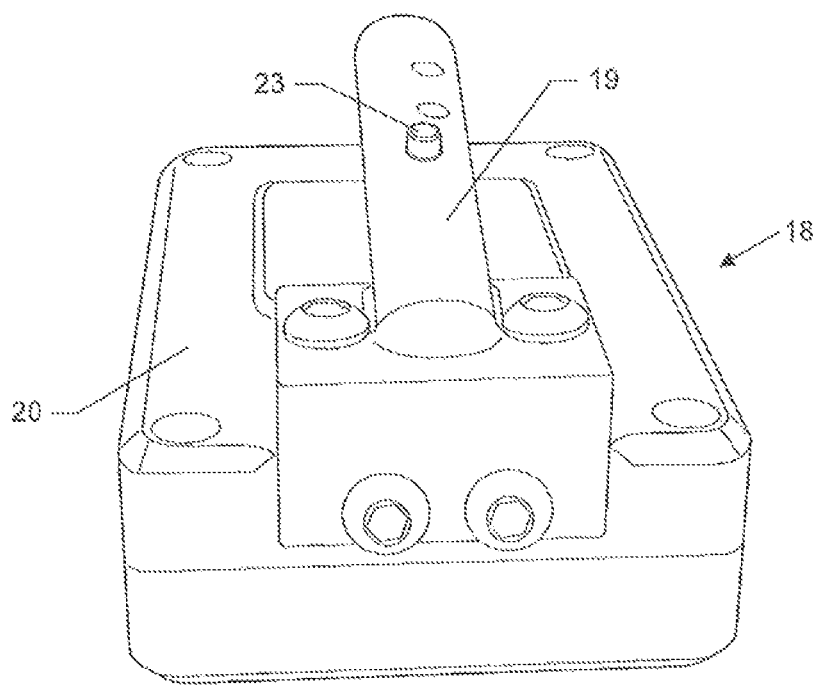
FIG. 4 is another under side perspective view of the embodiment of FIG. 3.
Figure 5:
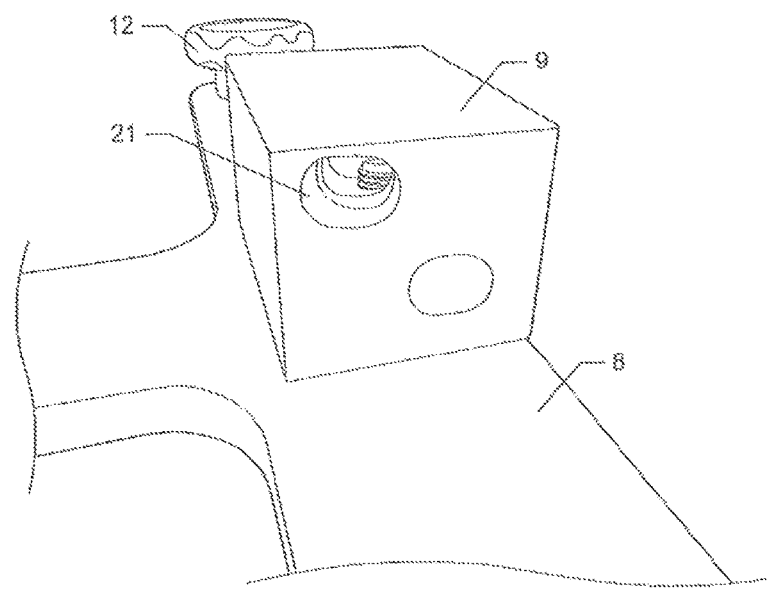
FIG. 5 is a detail partial perspective view of the docking station of the embodiment of FIG. 1.

As best shown in FIG. 3, the electronic orientation monitor 18 has a shaft 19 disposed on its underside 20 such that the shaft 19 extends from the underside 20 at an angle that is matched to a desired anteversion of the acetabular cup. In the illustrated embodiment this angle is 15°, although this may vary depending upon the patient's anatomy, the surgeon's preferences and/or upon the type of prosthetic acetabular cup that is to be used. If another anteversion angle is desired, then a different shaft having the desired angle may be affixed to the electronic orientation monitor 18. The shaft 19 is sized so as to mate with one of two possible holes 21 or 22 provided within the docking station 9. The shape and geometry of each hole 21 and 22 is such that each of them presents only one option for entry of the shaft 19. The orientations of the holes 21 and 22 are selected such that the holes correspond to the orientation of the shaft of a prosthetic insertion implement that is to be used during the subsequent insertion steps that are described in more detail below.

The angles at which the first and second holes 21 and 22 are drilled into the docking station 9 are selected as to match a desired inclination of the acetabular cup. In the illustrated embodiment this angle is 40°, although this may vary depending upon the patient's anatomy, the surgeon's preferences and/or upon the type of prosthetic acetabular cup that is to be used.

Figure 6:
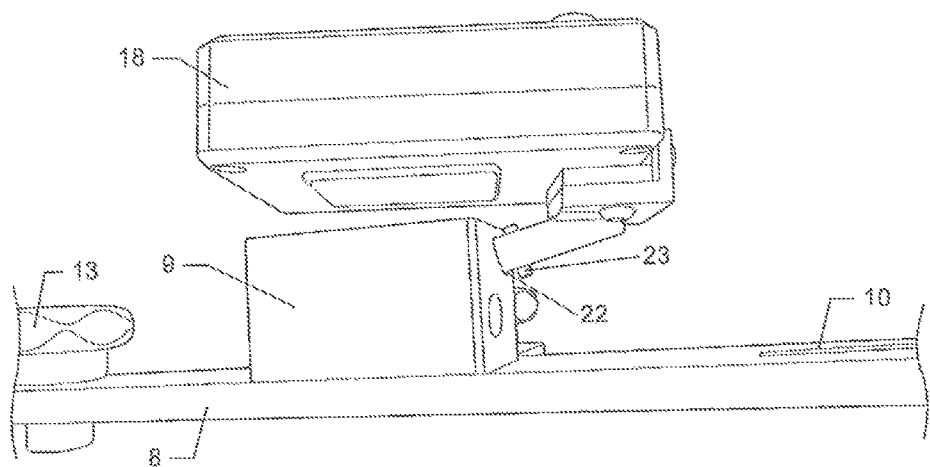
FIG. 6 is a detail partial perspective view of the electronic orientation monitor of FIG. 3 as attached to the docking station of the brace of FIG. 1.
Figure 7:
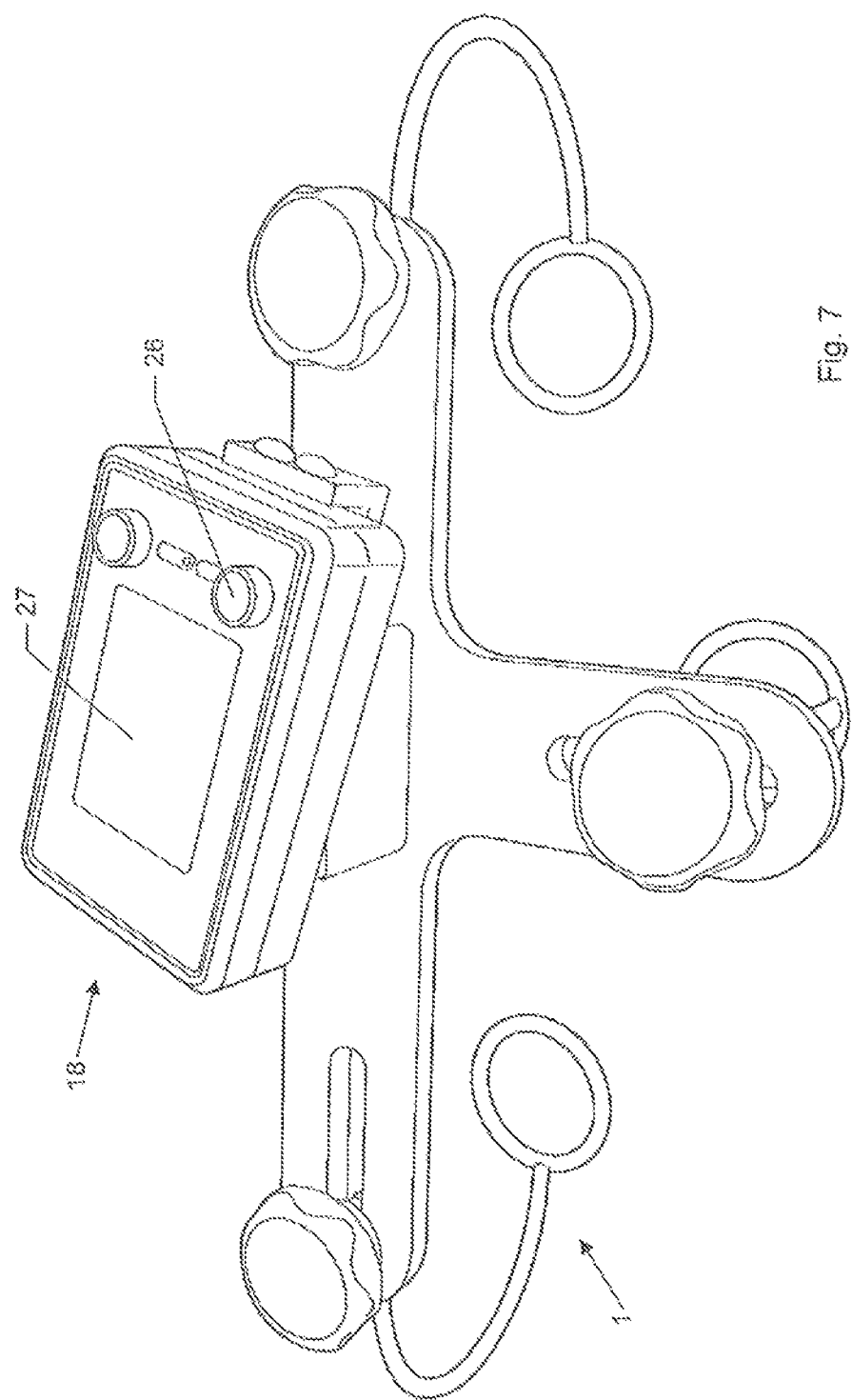
FIG. 7 is a top side perspective view of the electronic orientation monitor of FIG. 3 as attached to the docking station of the brace of FIG. 1.
Figure 8:
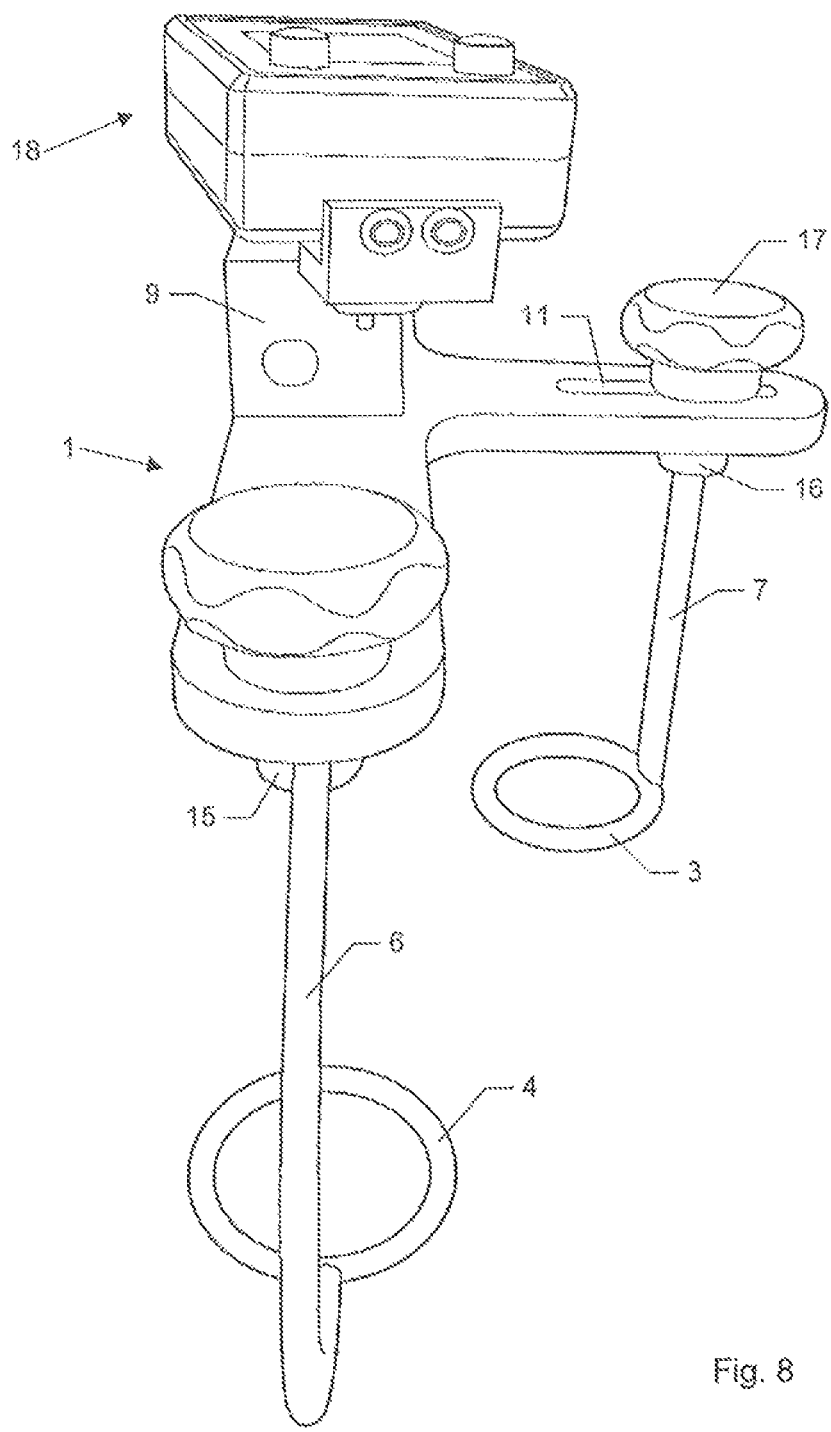
FIG. 8 is a side perspective view of the electronic orientation monitor of FIG. 3 as attached to the docking station of the brace of FIG. 1.

Mating the shaft with the first hole 21 provides a first docking configuration, as shown for example in FIG. 7. In the first docking configuration the orientation of the electronic orientation monitor 18 relative to the frame 8 is such that when the docking station 9 is in the reference orientation, the electronic orientation monitor 18 may be calibrated to a reference orientation that is suitable for insertion of an acetabular cup into the patient's left hand side acetabulum. Mating the shaft with the second hole 22 provides a second docking configuration, as shown for example in FIG. 6. In the second docking configuration the orientation of the electronic orientation monitor 18 relative to the frame 8 is such that when the docking station 9 is in the reference orientation, the electronic orientation monitor 18 may be calibrated to a reference orientation that is suitable for insertion of an acetabular cup into the patient's right hand side acetabulum.

The shaft 19 includes a pin 23, which functions as a stop when the shaft 19 is fully inserted into either the first hole 21 or the second hole 22. Additionally, the shaft 19 includes two ball bearing detents 24 and 25, which releasably retain the shaft 19 within the selected first or second hole 21 or 22 once it has been fully inserted.

As mentioned above, pushing the referencing apparatus 1 into engagement with the drapes on the patient causes the docking station 9 to assume the reference orientation relative to the patient's pelvis and hence the docked electronic orientation monitor 18 is in a reference orientation. Whilst in this state the user presses the calibration button 26, which prompts the electronic orientation monitor 18 to sense its current orientation. Data indicative of this reference orientation is stored within the memory of the electronic orientation monitor 18, which has now been calibrated and may be detached from the referencing apparatus 1. Additionally, the referencing apparatus 1 is now removed from the patient.

The electronic orientation monitor 18 is now attached to an insertion implement having either a trial acetabular cup, or the definitive acetabular cup. One such implement is disclosed in WO 2010/03111, however it will be appreciated that any suitable implement may be used. The surgeon manipulates the insertion implement into a position whereby the cup is adjacent the acetabulum and a display 27 on the electronic orientation monitor 18 guides the surgeon to orient the insertion implement such that the current orientation of the electronic orientation monitor 18 is equal to the reference orientation (or such that the current orientation has some other desired relationship to the reference orientation). Once the desired orientation has been achieved, the electronic orientation monitor 18 provides an indication to the surgeon, such as a visual indication on the display and/or an audible indication, and this prompts the surgeon to either assess the trial cup, or to impact the definitive cup into the patient's reamed acetabulum.

From the foregoing description it will be appreciated that the referencing apparatus 1 is configured for solely anterior engagement with the drapes that are on the patient during the steps of pressing the referencing apparatus into engagement with the surgical drapes and during calibration of the electronic orientation monitor. This compares favourably with the clamp disclosed in WO 2010/031111, which requires both anterior and posterior engagement with the patient. This is because it has been appreciated by the present inventor that in practice the clamp of WO 2010/031111 may cause an undesirable obstruction to the surgeon.

Whilst the invention has been described with reference to specific examples, those skilled in the art will appreciate than it may be embodied in many other forms.

The invention claimed is:

1. A referencing apparatus for application onto a patient at least partially covered by surgical drapes, the referencing apparatus including;
    a substantially T-shaped frame extending along two axes perpendicular to each other and having three ends, two of said three ends being located on a first axis of the perpendicular axes and a third end of said three ends is located on a second axis of the perpendicular axes; said frame having a top surface and a bottom surface opposite to the top surface and extending between the three ends and having a through opening extending from the top surface to the bottom surface at each of said three ends of the frame, at least one of said through openings being a slot;
    a plurality of locating elements, each of said locating elements being a circular loop having an interior defining a cavity extending through the circular loop for engagement with surgical drapes such that the surgical drapes are disposed intermediate the plurality of locating elements and a respective plurality of predefined anatomical sites on the pelvis of the patient;
    a docking station coupled to the top surface of said frame at the intersection of the first and second axes, and having an upstanding side perpendicular to the top surface of the frame and including first and second alignment holes extending therein at different orientations relative to each other, and whereby, in use, the apparatus is shaped such that said coupling of the docking station to the top surface of the frame causes said docking station to assume a reference orientation relative to the plurality of predefined anatomical sites;

a plurality of elongated members, two of said elongated members being arcuate and each defining a radius of curvature along its length, and a third of the elongated members being linear along its length;

each of said plurality of elongated members attached to a circumference of one of the circular loops at a distal end, and coupled to one of the ends of said frame at a proximal end extending through a corresponding one of said through openings and secured to the frame by a threaded fastener, such that when said plurality of elongated members are coupled to said frame by said threaded fasteners, said cavities extending through the circular loops open towards and face the bottom surface of said frame; and wherein the first hole has an inclination arranged in the docking station to match a desired inclination for an acetabular cup that is for insertion into the patient's left hand side acetabulum and the second hole has an inclination arranged in the docking station to match a desired inclination for an acetabular cup that is for insertion in the patient's right hand side acetabulum, and wherein each of the first and second alignment holes being sized and shaped to receive a shaft of an electronic orientation monitor.

2. The referencing apparatus according to claim 1, wherein each said loop has a diameter of between 30 mm and 70 mm.

3. The referencing apparatus according to claim 1, wherein the arcuate member has a radius of curvature of between 40 mm and 80 mm.

4. The referencing apparatus according to claim 1, wherein an attachment position of the elongated arcuate member coupled to the slot disposed within the frame is selectively adjustable.

5. The referencing apparatus according to claim 4, wherein the slot has a length of between 60 mm and 120 mm.

6. The referencing apparatus according to claim 4, wherein the arcuate member is attachable to the slot by a clamping action provided by a threaded fastener.

7. The referencing apparatus according to claim 1, wherein an electronic orientation monitor is dockable with the docking station in either a first docking configuration or a second docking configuration.

8. The referencing apparatus according to claim 7, wherein the first docking configuration defines a first orientation of the electronic orientation monitor relative to the referencing apparatus and wherein the second docking configuration defines a second orientation of the electronic orientation monitor relative to the referencing apparatus.

9. The referencing apparatus according to claim 7, wherein the first and second docking configurations are respectively defined by said first and second alignment holes on said docking station.

10. The referencing apparatus according to claim 1, wherein the apparatus is configured to solely engage the drapes anterior to the patient.

11. The referencing apparatus according to claim 1, where said arcuate member is rotatably attachable to said frame so as to define an axis of rotation.

12. The referencing apparatus according to claim 11, where said loop defines a center in axial alignment with said axis of rotation of an arcuate member to which it is attached.

* * * * *